July 30, 1968 E. H. SCANLON Plant Pat. 2,823

RED MAPLE TREE

Filed Sept. 30, 1966

INVENTOR
EDWARD H. SCANLON

BY Ely and Golrick
ATTORNEYS

United States Patent Office

Plant Pat. 2,823
Patented July 30, 1968

2,823
RED MAPLE TREE

Edward H. Scanlon, Olmsted Falls, Ohio, assignor to Edward H. Scanlon & Associates, Inc., a corporation of Ohio Filed Sept. 30, 1966, Ser. No. 583,489
1 Claim. (Cl. Plt.—51)

Figure 1:
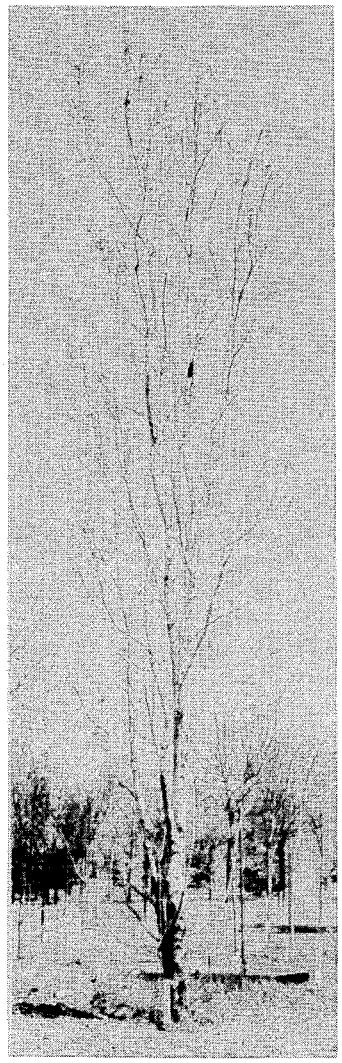

The present invention relates to a new and distinct variety of red maple tree (*Acer rubrum*) distinguished from the species and any varieties known to the applicant primarily by its tight, narrow columnar form and by the branching habit giving rise thereto.

Figure 2:
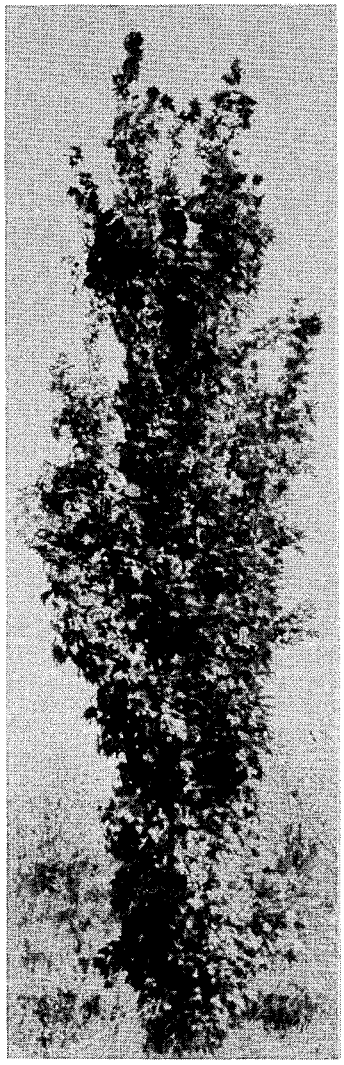

In the drawings:

FIG. 1 represents a tree of this new variety in dormant state to show its branching habit the more clearly and, as well its shape; and FIG. 2 represents the same tree in full foliage to show its characteristic and distinguishing shape.

This variety originated through applicant's observation of a red maple tree of interesting shape and two generations of its asexually reproduced propagules, in his nursery at Olmsted Falls, Ohio, to which the parent tree had been transplanted for preservation from nearby farmland. This new variety has been propagated by budding onto acer rubrum understock, and the hereinafter described distinguishing characteristics have been found to persist through two generations of propagules.

The red maple species has a shape which is quite variable and is described as having a normal outline wherein the crown tends to be umbrageous in spreading and undependable and not uniform as to shape and height. By contrast in the present variety the branches depart from the principal stem at about a twenty degree angle and then rise vertically, so that with the tree lacking a distinct leader the branches form a stiff tight column, presenting a very narrow silhouette, the angular relation of branches to trunk approximating somewhat, for example, the Lombardy poplar.

A branch forming on a dominant branch comes to rise sharply at such twenty degree angle and the dominant branch is then reduced in calipre with the younger branch sharing its vigor resulting in a slight curvature in each at the region of branching and thereby a contorted appearance.

The leaves of this new variety have the typical red maple size and outline (as described by Sargent, Manual of the Trees of North America) with deep and tightly V-shaped sinuses; have the thick leathery texture and very dark green upper surface usual in the northern strains of the northern tier of the United States and of Canada in contrast with the tissue-like lighter colored southern strains of the species. The lower surface is silvery, though not as pronounced as in the species.

More particularly this variety may be described as having been found to have the following characteristics, as set forth in Rehder, Manual of Cultivated Trees and Shrubs (2 ed.—1940), of the species *Acer rubrum:*

Branchlets: Glabrous with three to five leaves.

Leaves: 6–10 cm. long, subcordate in shape with triangular-ovate, short-acuminate unequally crenate-serrate lobes, dark green and lustrous above, glaucous beneath and usually pubescent on the veins.

Petiole: 5–10 cm. long, red.

Flowers: Slender-stalked and red with petals, which by observation of the new variety may be particularized as being brilliant scarlet and about three-eighths of an inch long.

I claim:

A new and distinct variety of red maple tree characterized primarily by its tight stiff narrow columnar shape approximating that of Lombardy poplar in silhouette, the shape originating from the branching habit wherein with the tree having no distinct leader, branches depart from a larger branch at a sharply acute angle on the order of about twenty degrees and then rise about vertically.

References Cited

Scanlon Tailored Trees, Wholesale List No. 15, Fall 1963-Spring 1964, page 23 relied on. (Copy at Examiner's desk in Group 332.)

ROBERT E. BAGWILL, *Primary Examiner.*